United States Patent [19]
Swenson et al.

[11] Patent Number: 5,422,178
[45] Date of Patent: Jun. 6, 1995

[54] ELASTIC FILM LAMINATE

[75] Inventors: Douglas A. Swenson, St. Paul; Herbert J. Fox, Maplewood, both of Minn.; Dennis L. Krueger, Hudson Township, St. Croix County, Wis.; Rochelle L. Lockridge, Maplewood, Minn.

[73] Assignee: Minnesota Mining and Manufacturing Company, St. Paul, Minn.

[21] Appl. No.: 249,538

[22] Filed: May 26, 1994

Related U.S. Application Data

[62] Division of Ser. No. 901,420, Jun. 19, 1992, Pat. No. 5,376,430.

[51] Int. Cl.$^6$ .............................................. B32B 7/12
[52] U.S. Cl. .................................. 428/343; 428/354; 428/910
[58] Field of Search ............... 428/152, 198, 910, 130, 428/167, 172, 181, 182, 186, 343, 354

[56] References Cited

U.S. PATENT DOCUMENTS

| | | | |
|---|---|---|---|
| 4,300,967 | 11/1981 | Sigl | 156/164 |
| 4,418,123 | 11/1983 | Bunnelle et al. | 428/152 |
| 4,486,192 | 12/1984 | Sigl | 604/385 |
| 4,880,706 | 11/1989 | Mazuera et al. | 428/910 |
| 4,938,753 | 7/1990 | Van Gompel et al. | 604/385.2 |
| 4,940,464 | 7/1990 | Van Gompel et al. | 604/396 |
| 4,958,757 | 9/1990 | Greenebaume, II | 222/394 |
| 5,156,793 | 10/1992 | Buell et al. | 264/288.8 |
| 5,332,616 | 7/1994 | Patrick et al. | 428/910 |

FOREIGN PATENT DOCUMENTS

| | | | |
|---|---|---|---|
| 2244422 | 12/1991 | United Kingdom | A61F 13/15 |
| WO91/07277 | 5/1991 | WIPO | B32B 5/04 |

Primary Examiner—James J. Bell
Attorney, Agent, or Firm—Gary L. Griswold; Walter N. Kirn; William J. Bond

[57] ABSTRACT

An elastic film is provided with non-elastic regions and elastic regions formed from a multi-layer film of an elastomeric layer and a relatively inelastic layer(s).

1 Claim, 2 Drawing Sheets

ELASTIC FILM LAMINATE

This is a division of application Ser. No. 07/901,420, Jun. 19, 1992, now U.S. Pat. No. 5,376,430.

FIELD OF THE INVENTION

The invention concerns elastomeric films and more specifically concerns an improved elastomeric laminate.

BACKGROUND

Elastomeric films have for some time been used and discussed in the literature with regard to their applications in disposable products, such as baby diapers and adult incontinent devices. These elastomeric webs or films are used primarily in the body hugging portions of garments. Many of these elastics are temperature-treated to provide for controlled elastic recovery. In diapers, for example, elastomeric bands are typically used in the waistband portions such as discussed in U.S. Pat. No. 4,681,580, issued to Reising et al., and Lash, U.S. Pat. No. 4,710,189. Both of these patents describe the use of elastomeric materials which have a heat stable and a heat unstable form. The heat unstable form is created by stretching the material when heated around its crystalline or second phase transition temperature followed by a rapid quenching to freeze in the heat unstable extended form. The heat unstable elastomeric film can then be applied to the, e.g., diaper and then heated to its heat stable elastomeric form.

Berger, U.S. Pat. No. 3,694,815, proposed a method for attaching a stretched relaxed elastic ribbon to a garment by stretching conventional elastic ribbons and immediately freezing the elastomeric material at relatively extreme low temperatures (e.g., well below ambient).

UK Pat. Application 2190406 A proposed maintaining a conventional elastomer in a stretched condition, while attaching it to the member to be shirred (e.g., a diaper), by a rigidifying member, which would then be removed or destroyed following the attachment procedure. As described, the elastomers are first stretched then applied to the rigidifying member in its stretched form.

Matray et al., UK Pat. 2,160,473, proposes an elastomer which will shrink at an elevated temperature (e.g., at or above 175° F. or 79.4° C.). The allegedly novel feature of this material, compared to the heat shrink materials discussed above, is that it does not require preheating or cold treatment during the stretching operation but rather could be stretched at ambient temperatures by a differential speed roll process or by "cold rolling". The polymer proposed was a copolymer having alternating segments of polyamidepolyether block polymers, commercially available under the trade name Pebax, particularly Pebax Extrusion grades 2533 and 3533.

Problems with these elastomeric films include the difficulties inherent in applying a stretched elastic film to a flexible substrate such as a disposable diaper. For example, these film elastics, after being attached to a flexible substrate, such as by adhesives, will place shear stresses on the attachment areas. This can result in the elastic detaching from the flexible substrate, particularly after repeated elongations.

In copending application Set. No. 07/438,593, filed 11/17/89, having a common assignee, there is disclosed an elastomeric laminate having at least one elastomeric layer and at least one skin layer which addresses some of the above-noted problems in the art.

Despite the numerous advantages in the materials of the copending application, there is room for improvement for some applications. In order to activate the nonelastomeric laminate into a state that will allow it to recover and become elastomeric, the laminate must be stretched a substantial amount, for many materials contemplated as useful for the skin and core layers. Further, when the elastic is applied to a garment, equally high stretch ratios are generally required to provide sufficient elastic force to functionally elasticize the garment. This is problematic for applications where low elastic stretch ratios would be desirable, for example, when high levels of gathering of a garment is undesirable or where required by manufacturing needs. There is also a need for elastics that will provide elasticity only in specified areas without requiring the application of separate discrete elastic elements at each area.

The desirability of obtaining elasticity in specified areas of a ribbon or tape-like substrate is illustrated by U.S. Patent Nos. 3,800,796, 4,834,820, 4,778,701 and 4,227,952, which disclose the use of composite materials designed to have specified areas of elasticity for use in diaper systems. However, these composites require complicated construction mechanisms to bring the diverse elements of the composite together and/or special procedures for their manufacture and use, that limit their general applicability.

SUMMARY OF THE INVENTION

The present invention relates to improved non-tacky, microtextured, multi-layer elastomeric laminates. The laminates of the present invention are comprised of am elastomeric polymeric core layer(s), which provides elastomeric properties to the laminate and one or more polymeric skin layers. Laminates can be prepared by coextrusion of the selected polymers for the skin and core layers or by application of one or more elastomer layer(s) onto one or more already formed skin layer(s). The novel, non-tacky microtextured laminate is obtained by stretching the laminate past the elastic limit of the skin layers and, while the laminate is stretched, selectively deactivating the elasticity of the laminate at predetermined regions. The laminate then recovers, in the non-deactivated regions, which can be instantaneous, over an extended time period, which is skin layer controllable, or by the application of heat, which is also skin layer controllable.

The selectively deactivated areas provide high-strength inelastic regions. The recovered regions can be microtextured or have detached skin layers.

DETAILED DESCRIPTION OF PREFERRED EMBODIMENTS OF THE INVENTION

The present invention relates broadly to novel non-tacky, multi-layer elastomeric laminates comprising at least one elastomeric core layer and at least one relatively nonelastomeric skin layer. The skin layer(s) are stretched beyond their elastic limit and recovered in selected, non-deactivated, areas with the core layer so as to form elastic regions. Microtexture or microstructure means that the layer contains peak and valley irregularities or folds which are large enough to be perceived by the unaided human eye as causing increased opacity over the opacity of the laminate before microtexturing, and which irregularities are small enough to be perceived as smooth or soft to human skin. Magnification of the irregularities is required to see the details of the microtexture.

The elastomer can broadly include any material which is capable of being formed into a thin film layer and exhibits elastomeric properties at ambient conditions. Elastomeric means that the material will substantially resume its original shape after being stretched. Further, preferably, the elastomer will sustain only small permanent set following deformation and relaxation, which set is preferably less than 20 percent and more preferably less than 10 percent of the original length at moderate elongation, e.g., about 400–500%. Generally, any elastomer is acceptable which is capable of being stretched to a degree that causes relatively consistent permanent deformation in a relatively inelastic skin layer. This can be as low as 50% elongation. Preferably, however, the elastomer is capable of undergoing up to 300 to 1200% elongation at room temperature, and most preferably up to 600 to 800% elongation at room temperature. The elastomer can be both pure elastomers and blends with an elastomeric phase or content that will still exhibit substantial elastomeric properties at room temperature.

Heat-shrink elastomers are contemplated for use in the present invention, however, non-heat-shrinkable elastomers can be used while retaining the advantages of heat shrinkability in selected embodiments. Non-heat-shrinkable means that the elastomer, when stretched, will substantially recover, sustaining only a small permanent set as discussed above. Non-heat-shrinkable polymers include block copolymers such as those known to those skilled in the art as A-B or A-B-A block copolymers. These block copolymers are described, for example, in U.S. Pat. Nos. 3,265,765; 3,562,356; 3,700,633; 4,116,917 and 4,156,673, the substance of which are incorporated herein by reference. Styrene/isoprene, butadiene or ethylene-butylene/styrene (SIS, SBS or SEBS) block copolymers are particularly useful. Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers are also contemplated.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric layer to a skin layer. Examples of tackifiers include aliphatic or aromatic hydrocarbon liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, reinforcing fiber, starch and metal salts for degradability or microfibers can also be used in the elastomeric core layer(s).

The skin layer can be formed of any semi-crystalline or amorphous polymer that is less elastic than the core layer(s) and will undergo permanent deformation at the stretch percentage that the elastomeric laminate will undergo. Therefore, slightly elastomeric compounds, such as some olefinic elastomers, e.g. ethylene-propylene elastomers or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate) (only in blends) and the like, and blends thereof. The skin layer material can be influenced by the type of elastomer selected. Skin-to-core layer contact in the FIG. 3 embodiment has been found to follow three modes; first, full contact between the elastomeric core layer and microtextured skin layer; second, full contact with cohesive failure of the core under the microtextured skin folds; and third, adhesive failure of the skin to the core under the microtexture folds with intermittent skin/core contact at the fold valleys.

The skin layer, preferably inelastic, used in conjunction with an elastomeric core layer will form at least one outer layer of the laminate. Used as either outer or inner layer, the skin layer will modify the elastic properties of the elastomeric laminate when in contact with the elastomeric layer by any of the three above-described modes.

Additives useful in the skin layer include, but are not limited to, mineral oil extenders, antistatic agents, pigments, dyes, antiblocking agents, provided in amounts less than about 15%, starch and metal salts for degradability and stabilizers such as those described for the elastomeric core layer.

Other layers may be added between the core layer and the outer layers, such as interlayers to either increase or decrease the bonding of the skin and core layers. Tie layers can be formed of, or compounded with, typical compounds for this use including maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatibilizers or delamination-promoting additives in one or more of the skin or core layers.

The shrink recovery mechanism of the laminate, after stretching and selective deactivation, depends on the conditions of film formation, the nature of the elastomeric layer(s), the nature of the skin layer(s), the manner in which the laminate film is stretched and the relative thicknesses of the elastomeric and skin layer(s). By controlling these variables, the laminate film can be designed to instantaneously recover, recover over time or recover upon heat activation. Generally, the core-to-single skin layer ratio will be at least 3, preferably, at least 5 and less than about 100 and most preferably at least 5 to about 75. The overall laminate thickness will be at least 1 mil, preferably at least 2 mils, although preferably less than 10 mils for cost and performance considerations. At core-to-skin layer ratios less than 3, the laminate has a tendency to not recover when stretched. A stretched and selectively deactivated laminate capable of instantaneous shrink is one in which the stretched, non-deactivated areas of the elastomeric laminate will recover more than 15% in 1 sec. A laminate capable of time shrink is one where the 15% recovery point takes place more than 1 sec., preferably more than 5 sec., most preferably more than 20 sec. after stretch, and a laminate capable of heat shrink is where less than 15% shrink recovery occurs to the laminate in the first 20 seconds after stretch and will remain capable of heat shrink for weeks after it is stretched. Percent recovery is the percent that the amount of shrinkage is of the stretched length minus the original length of the activated area. For heat-shrink laminates there will be an activation temperature which will initiate significant heat-activated recovery. The activation temperature used for a heat-shrink laminate will generally be the temperature that will yield 50% of the total possible recovery ($T_{a-50}$) and preferably this temperature is defined as the temperature which will yield 90% ($T_{a-90}$) of the total possible recovery. Total possible recovery includes the amount of preactivation shrinkage.

Generally, where the skin layer is relatively thin, the laminate will tend to contract or recover immediately in the non-deactivated areas. When the skin thickness is increased sufficiently the laminate can become heat shrinkable in the non-deactivated regions or areas. This phenomenon can occur even when the elastomeric layer is formed from a non-heat shrinkable material. By careful selection of the thicknesses of the elastomeric layer and the skin layer(s), the temperature at which the laminate recovers by a set amount can be controlled. This is termed skin controlled recovery, where generally by altering the thickness or composition of the skin, one can raise the elastic recovery activation temperature of an elastomeric core by a significant degree, generally more than at least 10° F. (5.6° C.) and preferably by 15° F. (8.3° C.) and more. Although any skin thickness which is effective can be employed, too thick a skin will cause the laminate to remain permanently set when stretched. Generally, where a single skin is less than 30% of the laminate this will not occur. For most heat or time shrink materials, the stretched nondeactivated regions of the elastomeric laminate must be cooled so that the energy released during stretching does not cause immediate heat activated elastic recovery. Fine tuning of the shrink recovery mechanism can be accomplished by the degree that the activated regions are stretched.

Figure 4:
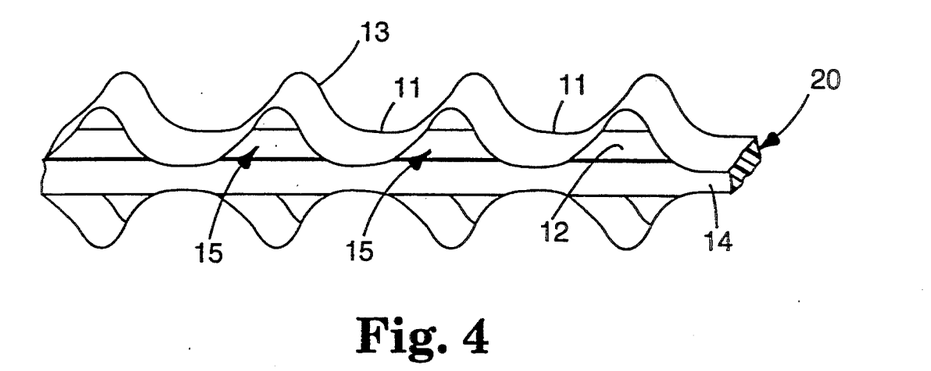
FIG. 4 is a perspective view of a delaminated skin embodiment of the invention.
Figure 6:
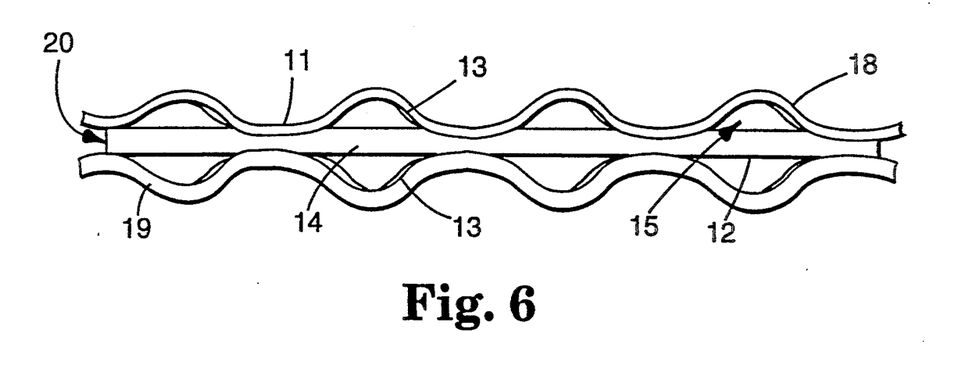
FIG. 6 is an end view of the FIG. 4 embodiment as it would appear in a diaper.

Improvements in the laminate structure of this invention over that of copending application U.S. Ser. No. 07/438,593 lie in a laminate film having elastic properties at selected regions or zones separated by thin, non-elastic regions or zones. The elastic regions or zones are characterized by a microtextured surface on the skin layers or, in a preferred embodiment, a thin, skin layer selectively secured to the elastomeric layer in the thin non-elastic regions or zones (FIG. 4). In this preferred embodiment, detached skin layer material 13 in the elastic zones or regions 12 allows the elastomeric core layer 14 to recover uninhibited without the skin layer 13 effecting the elastic properties. However, the skin layer 13 provides a continuous unstressed attachment surface for securing the elastic 20 to substrates to be elasticized, without having to directly adhere the elastic to the substrates (FIG. 6). Conventional methods of securing stressed elastic directly to a substrate are problematic. An elastic under stress when attached to a substrate creates shear forces that can cause detachment of the elastic, stress relaxation of the elastic or reduction in elastic properties. The FIG. 4 elastic 20 is not directly attached to the substrate when it is under stress. The elastic 20 can be easily and securely attached to a substrate while avoiding the above-noted problems with conventional elastic. The preferred elastic 20 of FIG. 4 further provides a breathable securement due to channels 15, particularly useful in garment applications.

The non-elastic regions 11 are characterized by a smooth layer of oriented skin layer material secured to a reduced thickness elastomeric core layer 14. The elastomeric core layer 14 is unstressed in this non-elastic region 11 and generally thinner than the elastomeric layer 14 in adjacent recovered elastic regions or zones 12. These non-elastic regions 11 provide secure unstressed attachment points for the elastic laminate 10 or 20. The non-elastic regions 11 also provide reinforcement zones between the elasticized regions reducing the possibility of deformation of the elastic laminate, or attached substrates, when under stress.

In the FIG. 4 embodiment, the elastic laminate 20 can be continuously secured to a substrate by the skin layer 13. However, the elastic regions will be unattached and free to contract with its full elastic force when stretched. The secured skin layer, in both the elastic regions 12 and non-elastic regions 11, will keep the elastic in place and also serve as a reinforcement element for the substrate to which the elastic 20 is attached.

Figure 3:
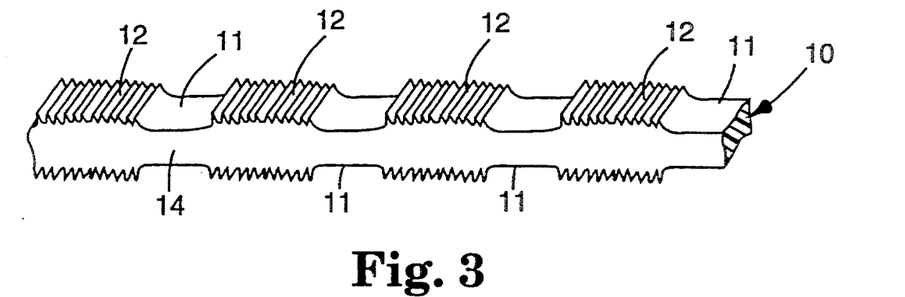
FIG. 3 is a perspective view of a microtextured skin embodiment of the invention.

With the FIG. 3 embodiment, the elastic regions 12 will be microtextured tending to create a mechanical release layer. The elastic of this embodiment can therefore be applied to substrates with a uniform adhesive coating. The elastic regions will then preferentially detach, allowing the elastic to stretch and elastically recover, while remaining securely attached to the substrate in the non-elastic zones or regions 11.

Figure 1:
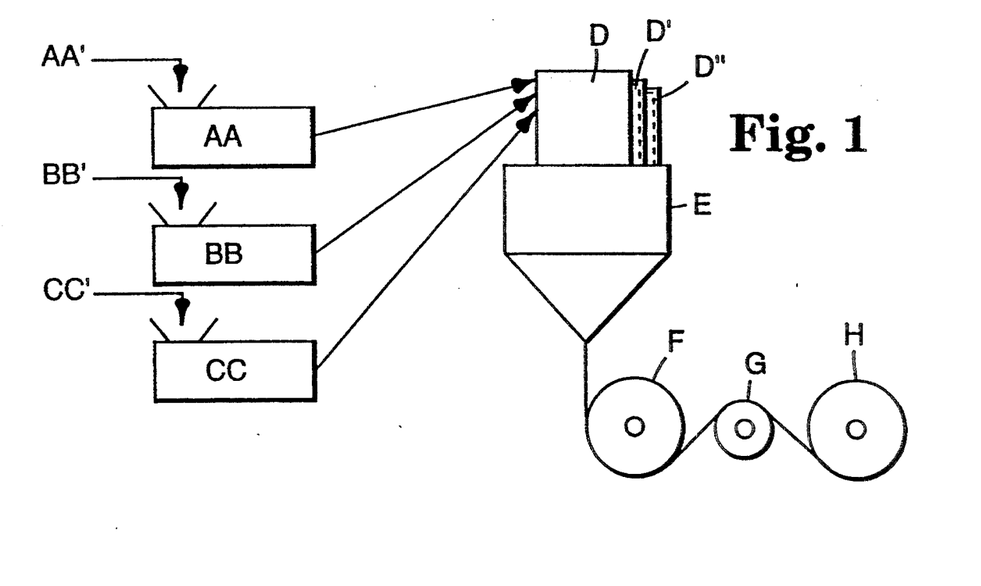
FIG. 1 is a schematic representation of a process and apparatus used to coextrude the laminates of the invention.

A preferred mechanism for forming the film laminate by extrusion is shown in FIG. 1 where D, D' and D" are feedblocks or manifolds. D, D' and D" can be separate or combined, or a part of die E. E is a conventional multiple layer die or a combining adapter and die such as disclosed in U.S. Pat. Nos. 4,152,387 or 4,197,069 (Cloeren). As shown, feedblocks or manifolds can be used to feed into each layer passageway of the multiple layer die E or to only a single passageway of such a die (e.g., with a combining adaptor in the feedblock region). AA, BB, and CC are extruders. AA', BB' and CC' are streams of thermoplastic material being extruded into the feedblocks or manifold die. E is the 3 or more layer (e.g., 5-layer) die, F is a heated casting roll, and G and H are rolls to facilitate take-off and roll-up of the laminate. Nip rollers can also be provided.

The die and feedblock used are typically heated to facilitate polymer flow and layer adhesion. The temperature of the die depends upon the polymers employed and the subsequent heat treatment steps. Generally the temperature of the die is not critical but temperatures are generally in the range of 350 to 550° F. (176.7° to 287.8° C.) with the polymers exemplified.

Whether the laminate is prepared by coating, lamination, sequential extrusion, coextrusion or a combination thereof, the laminate formed and its layers will preferably have substantially uniform thicknesses across the laminate. Laminates prepared in this manner have generally uniform properties with a minimum of edge effects such as curl, modulus change, fraying and the like. After formation, the laminate is stretched past the elastic limit of the skin layer(s), which deform. The stretched laminate is then subjected to localized heat treatment to selectively relax or deactivate the elastic in certain regions or zones. This allows the oriented elastic in the treated regions to locally randomize to form a dimensionally stable elastic material in these regions or zones. The localized heat treatment must be long enough to release stresses in the deformed unstable elastic.

The now localized heat treated laminate is recovered, as discussed above in the non-heat treated, or non-deactivated, regions or zones. For heat-activated recovery, the inherent temperature of heat activation is determined by the materials used to form the elastic layer of the laminate in the first instance. However, for any particular laminate the activation temperature, for example, either $T_{a\text{-}50}$ or $T_{a\text{-}90}$, can be adjusted by varying the skin/core ratio of the laminate, adjusting the percent stretch or the overall laminate thickness. The activation temperature used for a heat-shrink laminate is generally at least 80° F. (26.7° C. ), preferably at least 90° F. (32.2° C.) and most preferably over 100° F. (37.8° C.). When forming a heat activatable laminate, the stretched and locally heat treated laminates are quenched on a cooling roller, which prevents the heat generated during elongation from prematurely activating laminate recovery in the remaining activated regions. The chill roll temperature is maintained below the activation temperature.

Figure 2:
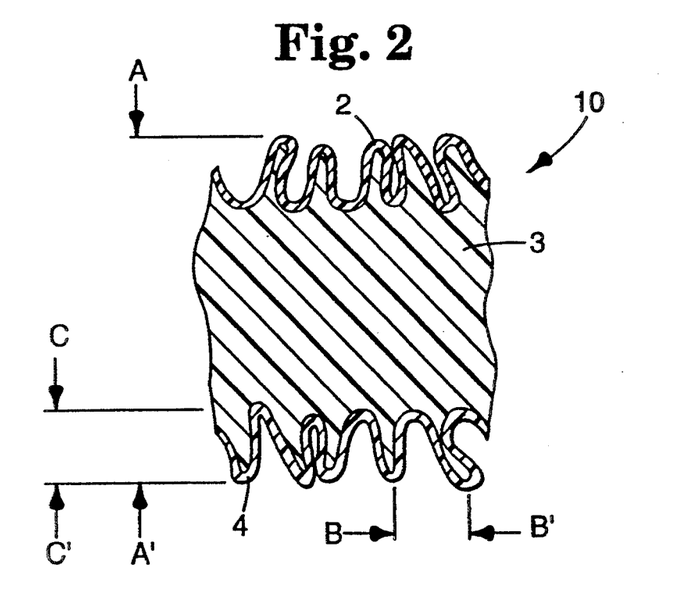
FIG. 2 is the cross-sectional segment of a laminate with microstructuring caused by uniaxially stretching a film of the invention.

FIG. 2 is a schematic diagram of the common dimensions which are variable for uniaxially stretched and recovered laminates in the activated or recovered microtextured regions. The general texture is a series of regular repeating folds. These variables are the total height A-A' the peak to peak distance B-B' and the peak to valley distance C-C'. These variables were measured for a series of polyolefin/styrene-isoprene-styrene/polyolefin laminates General ranges for A-A', B-B' and C-C' were noted. For total height (A-A' ), the range measured was from 0.79 to 32 mils(0.02 to 0.81 mm). For peak-to-peak distance (B-B'), or the fold period, the measured range was from 0.79 to 11.8 mils(0.02 to 0.30 mm). For peak-to-valley distance (C-C'), the measured range was from 0.04 to 19.7 mils(0.001 to 0.5 mm).

The elastomeric laminates prepared in accordance with the invention, can also be described in terms of increase in skin surface area. Where the microtextured laminate shows heavy textures, the surface area will increase significantly. As the stretch ratio increases, so does the percent increase in surface area, from the unstretched to the stretched and recovered laminate. Generally, the skin surface area will increase by at least 50%, preferably by at least 100% and most preferably by at least 250% in the stretch and recovered areas or regions. The increase in surface area directly contributes to the overall loft, texture and feel of the laminate surface when microstructured or when the skin detaches from the elastic core.

For those constructions prone to delamination, a brief relaxing or annealing following activation may be used to counteract this tendency, if desired. This brief annealing step will release residual unstable orientation at the elastomeric layer and skin layer interface, particularly for elastic between folds of the microstructured skin layer. The annealing would generally be above the glass transition point temperature ($T_g$) of the elastomer, above the B block $T_g$ for ABA block copolymers, but below the skin polymer melting point. A lower annealing temperature is generally sufficient. The annealing will generally be for longer than 0.1 seconds, depending on the annealing temperature, followed by cooling to room temperature in the relaxed annealed state. With commercial ABA block copolymers (e.g., Kraton TM 1107), an annealing or relaxing temperature of about 75° C. is found to be sufficient. If it is preferred to create delamination of the skin in the elastic regions, this annealing step should be avoided prior to delamination.

FIG. 3 is an example of a film that has been stretched and locally heat treated to create nonelastic deactivated regions 11 and allowed to recover in elastic regions 12. The elastic has been locally heat treated as bands extending transverse to the stretch direction. However, the localized heat treatment and deactivation can extend in bands in the elongation direction, multiply directions or in patterns to create elastics where the localized heat treated deactivated regions or zones can selectively buckle. In FIG. 3, the elastic regions 12 of the elastic laminate 10 have microtextured skin layers.

In some embodiments, the skin layer can be selectively detached in the activated elastic areas 12 to form the elastic regions 12 of FIG. 4 by, e.g., working the film in conjunction with a delaminating heat treatment. This detachment process is dependent on the relative adhesiveness of the skin and core layers and the thickness of the skin and core layers. Additives can be added to the skin and/or core layers to promote delamination, such as polymers or release agents incompatible with the polymer in the adjacent layer that tends to separate the interlayer interface. For example, it has been found that polystyrene and oil added to an A-B block copolymer core promote delamination of polyolefin skin layers, while ethylene vinyl acetate or polyalphamethylstyrene added to the polyolefin skin layers also promotes delamination.

FIG. 4 displays the embodiment where the skin layer 13 is selectively detached from the elastomeric core layer 14. In the locally heat-treated non-elastic regions 11, the oriented skin layer 13 remains securely bonded to the elastomeric core layer 14, as well as strengthened due to the orientation and subsequent localized heat treatment. The elastomeric core layer 14 in regions 11 (as in FIG. 3) is thin relative to the elastomeric core layer in elastic regions 12. The detached skin layer 13 in elastic regions 12 provides an attachment surface in the elastic regions 12 while avoiding the above discussed problematic direct attachment of a substrate to the elastomeric layer 14.

The FIG. 4 elastic 20 also provides air channels 15. These channels 15 can provide breathability to elasticized regions of a garment, or the like, such as a cuff or diaper waistband or legband.

The laminate of FIGS. 3 and 4 can be extensively used in disposable diapers, for example as a waistband, located in either the front or side portions of the diaper at waist level, as leg elastic, as an outer cover sheet or in elasticated slip-on diapers or training pants, where the elastomeric laminate could be used as, or in, side panels around the hip that have zones of elasticity to create a tight fitting garment. The laminates can be applied as continuous or intermittent lengths by conventional methods. When applied, a particular advantage of the elastic laminate 20 with delaminated skin (e.g., the FIG. 4 embodiment), is that extremely uniform shirring can be easily obtained by applying elastic laminates with substantially flat non-elastic regions 11 while the elastic regions 12 are stretched. When the elastic regions 12 recover, the FIG. 6 garment layers 18 and 19 will shirr only in those regions with skin delamination, i.e. the elastic regions 12, and shirr uniformly in elastic regions 12 (i.e., as a single gather). This allows one to predictably and easily control garment shirring, a property not possible with conventional film elastics.

Similar uniform shirring can be obtained with the FIG. 3 embodiment by zone release coating the elastic laminate 10 in elastic regions 12. The release coating can be a conventional low adhesion coating or in a preferred arrangement an oil, such as mineral oil. The oil is preferred due to cost and ease of application. The oil has not been found to migrate when the elastic 10 is wound in a roll form as would be expected for a conventional film. It is believed that oil migration is arrested by the microtextured skin layer surface in the oil-coated area.

When an elastic laminate with flat non-elastic regions 11 as shown in FIGS. 3 and 4, is attached to a garment; as shown in FIG. 6, the elastic also provides improved elastic stress at low elongations of the elastic laminate 10, versus a continuous elastic film. The elongational stresses in this arrangement are preferentially confined to the elastic regions which proportionally provide increased elastic stress or force.

The elastomeric laminate can be adhered to a garment by ultrasonic welding, heat sealing and adhesives such as pressure-sensitive adhesives, by conventional methods. The adherence would be preferably in at least the locally heat treated non-elastic regions 11.

Figure 5:
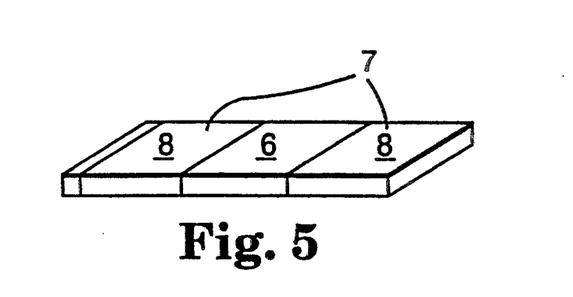
FIG. 5 is a diaper tape tab formed of the invention laminate.

Another use for the invention laminates would be as an elasticized diaper fastening tab as per, e.g., U.S. Pat. No. 3,800,796, as shown in FIG. 5. The elastic zone 6 can be placed at the desired location while providing selectively deactivated non-elastic end regions 7 and an elastic central region 6. Adhesive 8 could then be applied to one or more faces of the inelastic end regions 7.

A further embodiment of the invention is an anisotropic film that will be non-elastic on a first axis and elastic or extensible on an axis orthogonal to the first axis. The film non-elastic axis is provided by stretching an elastic laminate, then subjecting the entire stretched laminate to a deactivating heat treatment rather than merely a localized deactivating heat treatment. The skin layer will then be oriented and strengthened in the direction or axis of stretch and substantially nonextensible on this axis. However, the film in the orthogonal or cross direction will be readily extensible or elastic, if subsequently stretched and allowed to recover. This anisotropic quality renders this film particularly well suited to applications where a film is desired that is strong in one direction yet conformable in the cross direction. For example, a sealing pressure-sensitive adhesive tape to be applied to an uneven surface such as a pipe fitting or screw threads is advantageously conformable in the cross direction to sealingly engage all surfaces, despite their variation in diameter, yet strong in the longitudinal direction.

The following Examples are provided to illustrate presently contemplated preferred embodiments and the best mode for practicing the invention, but are not intended to be limiting thereof.

EXAMPLES

A continuous coextrusion process was carried out to prepare three layer film laminates having two outer inelastic skin layers and an elastomeric core layer. One extruder was used to feed the elastomeric core layer material and a second extruder was used to feed the inelastic skin layer material into a three-layer Cloeren TM feedblock, and the resulting layered melt was extruded through a single manifold film die and cast onto a cast roll. Feedblock and die temperatures ranged from approximately 400–540 deg F. (204–282 deg C. ) and the cast roll temperatures ranged from approximately 70–180 deg F. (21–82 deg C.). Line speeds averaged approximately 30 feet (9.14 m) per minute. Film laminate total thicknesses ranged from 3–10 mils (0.076–0.254 mm) and core to skin (C/S) ratios varied from 4:1 to 10:1. Film compositions, feedblock and die temperatures, cast roll temperatures, C/S ratios and total film thicknesses (in mils) are given in Table I.

A localized heat treatment was used to create non-elastic regions or zones on the elastic laminates. A three inch (7.62 cm) wide sample of film was first stretched in the transverse direction (TD) at a ratio of from about 3:1 to 6:1 and then was passed over a patterned heated roll which resulted in parallel longitudinal bands of inelastic regions running in the machine direction (MD) of the film. Heating temperatures ranged from about 150–180 deg F. (66–82 deg C.).

A cyclical stretching and heating process was used to affect delamination of the outer inelastic skin layers from the elastomeric core layer in the elasticized regions of the film laminates. A 1.0 inch ×3.0 inch (2.54 cm×7.62 cm) sample (MD by TD) of film was stretched in the transverse direction to just before break (95–150%), which activated the locally non-heat treated regions. The film was then placed in a stream of hot air supplied by a heat gun (approximately 140 deg F. or 60 deg C.). The film was heated until the elasticized regions were fully contracted and warmed (<1 minute). The film was then removed from the heat and was stretched by hand in the transverse direction until just before break, and then immediately allowed to recover. The film was heated once again (<1 minute), then was cyclically stretched and immediately released, in the transverse direction. This heating and stretching process was repeated until an observation of delamination or no delamination could be made. Delamination occurring after 3–10 cycles was considered excellent. The extent of delamination was evaluated visually and was classified as no delamination (0), delamination difficult (1), good delamination (2), delaminates easily, or excellent (3), and delaminates very easily (4). Delamination observations are given in Table II.

TABLE I

| Ex. | Skin Composition | Core Composition | Additives in Core | C/S Ratio | Film Thickness | Feedblock & Die Temp. (°F.) | Cast Roll Temp. (°F.) |
|---|---|---|---|---|---|---|---|
| 1 | PP 3085 | K-1657 | NONE | 10 | 3 | 450 | 80 |
| 2 | PP 1024 | K-1657 | NONE | 10 | 3 | 450 | 72 |
| 3 | PP 1024 | K-1657 | 10% PS-G3 | 7 | 3 | 450 | 80 |
| 4 | PP 1024 | K-1657 | 10% PS-666 | 7 | 3 | 450 | 120 |
| 5 | PP 1024 | K-1657 | 15% PS-666 | 7 | 3 | 450 | 120 |
| 6 | PP 1024 | K-1657 | 20% PS-666 | 7 | 3 | 450 | 120 |
| 7 | PP 1024 | K-1657 | 10% PS-615 | 5 | 3.5 | 450 | 180 |
| 8 | PP 1024 | K-1657 | 10% PS-615 | 7 | 3.5 | 450 | 180 |
| 9 | PP 1024 | K-1657 | 10% PS-615 | 7 | 3.5 | 450 | 120 |
| 10 | PP 1024 | K-1657 | 10% PS-615 | 7 | 3.5 | 450 | 80 |
| 11 | PP 1024 | K-1107 | 10% PS-615 + 1% IRGANOX 1076 | 5 | 3 | 400 | 80 |
| 12 | PP 3445 | K-1107 | 10% PS-615 + 1% IRGANOX 1076 | 5 | 3.3 | 420 | 70 |
| 13 | PP 3085 | K-1107 | 10% PS-615 + 1% IRGANOX 1076 | 5.5 | 3.5 | 411 | 80 |
| 14 | PP 3085 | K-1107 | 10% PS-615 + 1% IRGANOX 1076 | 5.5 | 3.5 | 435 | 80 |
| 15 | PP 3085 | K-1107 | 10% PS-615 + 1% IRGANOX 1076 | 5.5 | 3.5 | 460 | 80 |
| 16 | PP 3085 | K-1107 | 10% PS-615 + 1% IRGANOX 1076 | 5.5 | 3.5 | 480 | 80 |
| 17 | PP 3085 | K-1107 | 10% PS-615 + 1% IRGANOX 1076 | 5.5 | 3.5 | 500 | 80 |
| 18 | PP 3085 | K-1107 | 10% PS-615 + 1% IRGANOX 1076 | 5.5 | 3.5 | 520 | 80 |
| 19 | PP 3085 | K-1107 | 10% PS-615 + 1% IRGANOX 1076 | 5.5 | 3.5 | 540 | 80 |
| 20 | PP 3085 | K-1107 | 10% PS-615 + 1% IRGANOX 1076 | 7 | 3 | 420 | 70 |
| 21 | PP 3085 | K-1107 | 10% PS-615 + 1% IRGANOX 1076 | 7 | 3 | 480 MELT | 70 |
| 22 | PP 3085 | K-1107 | 10% PS-615 + 1% IRGANOX 1076 | 5 | 3 | 480 MELT | 70 |
| 23 | PP 1024 | K-1657 | 5% MINERAL OIL | 7 | 3 | 450 | 80 |
| 24 | PP 3085 | K-1107 | 5% MINERAL OIL + 1% IRGANOX 1076 | 7 | 2.5 | 420 | 70 |
| 25 | LDPE 4012 | K-1107 | 10% PS-615 + 1% IRGANOX | 7 | 2.5 | 420 | 70 |

TABLE I-continued

| Ex. | Skin Composition | Core Composition | Additives in Core | C/S Ratio | Film Thickness | Feedblock & Die Temp. (°F.) | Cast Roll Temp. (°F.) |
|---|---|---|---|---|---|---|---|
| 26 | HDPE 52053 | K-1107 | 10% PS-615 + 1% IRGANOX 1076 | 7 | 2.5 | 420 | 70 |
| 27 | PP 1024 | K-1657 | 10% PS-615 | 5 | 3.5 | 450 | 120 |
| 28 | 90% PP 1024 + 10% EVA 260 | K-1657 | 10% PS-615 | 5 | 3 | 450 | 120 |
| 29 | PP 3085 | K-1107 | 10% PS-615 + 1% IRGANOX 1076 | 5 | 3 | 450 | 70 |
| 30 | 95% PP 3085 + 5% EVA 260 | K-1107 | 10% PS-615 + 1% IRGANOX 1076 | 5 | 3 | 450 | 70 |
| 31 | PP 3085 | K-1657 | 10% PS-615 + 1% IRGANOX 1076 | 5 | 3 | 450 | 64 |
| 32 | 95% PP 3085 + 5% EVA 260 | K-1657 | 10% PS-615 + 1% IRGANOX 1076 | 5 | 3 | 450 | 64 |
| 33 | 90% PP 3085 + 10% PAMS 18-29 | K-1107 | 10% PS-615 + 1% IRGANOX 1076 | 5 | 3 | 450 | 70 |
| 34 | PP 3085 | PU 2102-75A | NONE | 5 | 3 | 435 | 80 |

Tensile and elongation data (ASTM D-638 and D-412) were obtained on the samples using an Instron 1122 Tensile Tester (available from Instron™ Corporation). A 0.5"×3.0"(1.27 cm×7.62 cm) sample was placed at a 2.0 inch (5.08 cm) gauge length and was stretched at a rate of 12 inches (30.5 cm) per minute. The tensile and elongation data are given in Table II.

TABLE II

| Ex. | Delamination | Tensile (MD) PSI at Break | Elongation (MD) % at Break | Tensile (TD) PSI at Break | Elongation (TD) % at Break |
|---|---|---|---|---|---|
| 1 | 1 | 574 | 903 | 690 | 818 |
| 2 | 0 | 767 | 859 | 666 | 844 |
| 3 | 2 | 2446 | 800 | 3018 | 793 |
| 4 | 2 | 2801 | 901 | 2592 | 823 |
| 5 | 2 | 2973 | 886 | 2961 | 863 |
| 6 | 2 | 2498 | 766 | 2243 | 816 |
| 7 | 1 | 2352 | 697 | 3263 | 722 |
| 8 | 1-2 | 2586 | 820 | 3526 | 847 |
| 9 | 2 | 2514 | 843 | 3160 | 812 |
| 10 | 1 | 2351 | 817 | 2502 | 793 |
| 11 | 3 | 2137 | 739 | 1884 | 706 |
| 12 | 3 | 1818 | 878 | 1114 | 615 |
| 13 | 3 | 1893 | 809 | 1828 | 695 |
| 14 | 3 | 1796 | 772 | 1969 | 757 |
| 15 | 3 | 1841 | 834 | 1777 | 737 |
| 16 | 3 | 1796 | 868 | 1256 | 601 |
| 17 | 3 | 1755 | 878 | 1664 | 781 |
| 18 | 3 | 1353 | 868 | 1144 | 611 |
| 19 | 3 | 1440 | 770 | 1112 | 559 |
| 20 | 4 | 1209 | 670 | 1389 | 857 |
| 21 | 4 | 1476 | 812 | 1338 | 849 |
| 22 | 3 | 1442 | 732 | 1286 | 766 |
| 23 | 2 | 1407 | 754 | 1928 | 812 |
| 24 | 4 | | | | |
| 25 | 2 | | | | |
| 26 | 4 | | | | |
| 27 | 1 | 1883 | 680 | 2514 | 729 |
| 28 | 3 | 2484 | 753 | 2904 | 727 |
| 29 | 3 | 1661 | 800 | 1511 | 863 |
| 30 | 4 | 1602 | 794 | 1566 | 901 |
| 31 | 1 | 2555 | 808 | 2124 | 756 |
| 32 | 2 | 2666 | 828 | 2541 | 773 |
| 33 | 4 | 1878 | 873 | 1199 | 775 |
| 34 | 2 | 3132 | 589 | 1343 | 355 |

The following abbreviations are used in Table I to indicate the materials used in the skin and core layers.

PP 3085 is Escorene™ 3085, a 36 MFI polypropylene available from Exxon Corporation.

PP 3445 is Escorene™ 3445, a 35 MFI polypropylene available from Exxon Corporation.

PP 1024 is Escorene™ 1024, a 12 MFI polypropylene available from Exxon Corporation.

LDPE 4012 is low density polyethylene #4012 available from Dow Chemical Company.

HDPE 52053 is high density polyethylene #52053 available from Dow Chemical Company.

K-1657 is Kraton™ G-1657 a styrene-ethylene-butylene-styrene (SEBS) block copolymer available from Shell Chemical Company.

K-1107 is Kraton™ 1107 a styrene-isoprene-styrene (SIS) block copolymer available from Shell Chemical Company.

PU 2102-75A is Pellathane TM 2102-75A, a polyurethane available from Dow Chemical Company.

PS-G3 is polystyrene #G3 available from Amoco Oil Company.

PS-666 is polystyrene #666 available from Dow Chemical Company.

PS-615 is polystyrene #615 available from Dow Chemical Company.

EVA 260 is Elvax TM 660, an ethylene-vinyl acetate copolymer available from I.E. dupont de Nemours Company.

PAMS 18-290 is poly(alphamethylstyrene) #18-290 available from Amoco Oil Company.

Irganox TM 1076 is an anti-oxidant available from Ciba-Giegy Corporation.

Amoco TM White mineral oil #31USP is mineral oil available from Amoco Oil Company.

Examples 1 and 2 are film laminates having two outer inelastic layers of polypropylene and a elastomeric core layer of a styrene-ethylene-butylene-styrene (SEBS) block copolymer. Two different polypropylenes were used. The inelastic skin layers delaminated from the elastomeric core layer in the elasticized regions of the film laminate having PP 3085 as the inelastic skin layers but delamination was difficult. No delamination was observed for the sample having PP 1024 as the inelastic skin layers.

Examples 3-12 show that the addition of a stiffening aid, polystyrene, to the elastomeric core layer promotes delamination.

Examples 4-6 are examples of the effect of varying the amount of polystyrene added to the elastomeric core. No significant effects on the delamination characteristics or elastic properties of the film laminates were observed by varying the amount of polystyrene from 10-20 weight percent. In Examples 8-10 the cast roll temperature was varied from 80-180 deg F. (27-82 deg C.). Raising the cast roll temperature above 120 deg F. (49 deg C.) did not influence delamination.

Examples 13-19 are film laminates having two outer inelastic layers of PP 3085 polypropylene and an elastomeric core layer of a styrene-isoprene-styrene (SIS) block copolymer having 10 weight percent polystyrene in the core. The skin layers easily delaminated from the elastomeric core layers for these samples. These examples also demonstrate that increasing the feedblock and die temperatures does not influence the delamination properties of the film laminates.

Examples 7, 8, 21 and 22 show that film laminates having a higher core-to-skin ratios (7:1) delaminate more readily than those with a lower core-to-skin ratios (5:1).

Examples 23 and 24 show the effect of adding mineral oil to the elastomeric core. These samples delaminated more readily than samples having elastomeric cores without any oil additive.

Examples 25 and 26 are film laminates having two outer inelastic layers of polyethylene and an elastomeric core layer of a styrene-isoprene-styrene (SIS) block copolymer having 10 weight percent polystyrene in the core. The use of high density polyethylene and low density polyethylene as the skin layers was investigated. The skin layers easily delaminated from the elastomeric core layers for these samples.

Examples 27-32 show that the addition of 5 and 10 weight percent of an ethylene vinyl-acetate copolymer to polypropylene skin layers promotes delamination. A comparison of Examples 29 and 30 to Examples 31 and 32 also shows that delamination occurs more readily when the elastomeric core is a styrene-isoprene-styrene block copolymer than it does when the core is a styrene-ethylene-butylene-styrene block copolymer.

Examples 29 and 33 show that the addition of 10 weight percent of poly(alphamethylstyrene) to polypropylene skin layers promotes delamination.

Example 34 is a film laminate having two outer inelastic layers of polypropylene and a polyurethane elastomeric core layer. This sample showed good delamination characteristics.

We claim:

1. An anisotropic film laminate pressure-sensitive adhesive tape comprising a film laminate having a first face and a second face said film laminate comprising a continuous elastomeric core layer and at least one continuous inelastic skin layer or uniaxially oriented plastic, the film laminate being substantially inelastic in, the direction of orientation of said at least one skin layer said skin layer being unoriented in a direction transverse to said direction of orientation such that the laminate is extensible in said transverse direction, said laminate on at least one of said first face or said second face further comprising a pressure-sensitive adhesive layer so as to form a pressure-sensitive adhesive tape.

* * * * *

UNITED STATES PATENT AND TRADEMARK OFFICE
CERTIFICATE OF CORRECTION

PATENT NO.: 5,422,178

DATED: June 6, 1995

INVENTOR(S): Douglas A. Swenson et al.

It is certified that error appears in the above-identified patent and that said Letters Patent is hereby corrected as shown below:

Col. 1, line 66, "Set." should read --Ser.--;

Col. 4, line 7, "photostabilizers,." should read --photostabilizers,--;

Col. 4, line 33, "of,the" should read --of the--;

Col. 4, line 38, "either outer" should read --either an outer--;

Col. 5, line 53, "nondeactivated" should read --non-deactivated--;

Col. 7, line 49, "laminates General" should read --laminates. General--.

Signed and Sealed this

Twenty-second Day of October, 1996

Attest:

BRUCE LEHMAN

*Attesting Officer*     *Commissioner of Patents and Trademarks*